Figure 1:
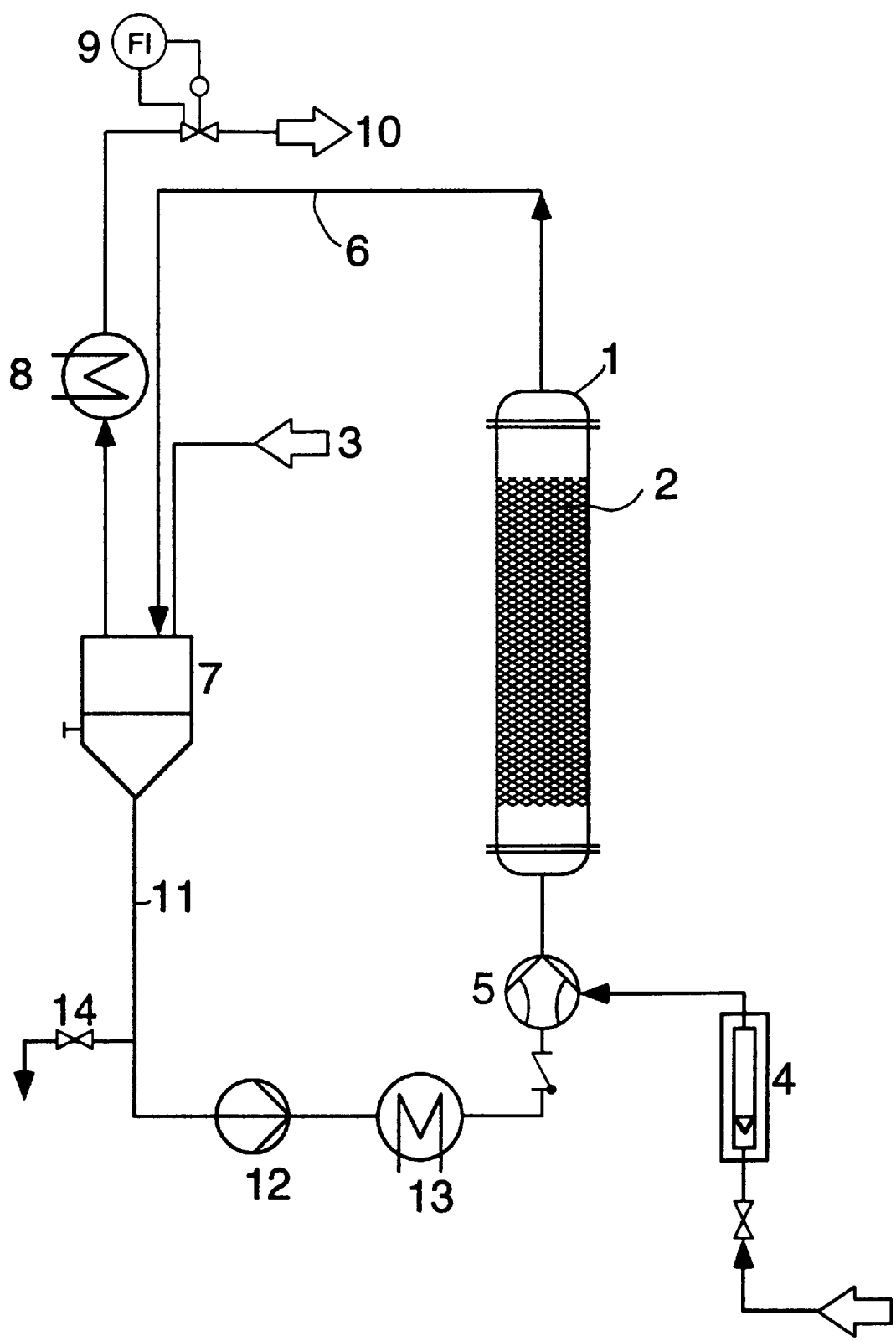

United States Patent [19]
Kaibel et al.

[11] Patent Number: 5,939,589
[45] Date of Patent: Aug. 17, 1999

[54] PROCESS AND REACTOR FOR CARRYING OUT CONVERSION WITH CATALYSTS SUSPENDED IN LIQUIDS

[75] Inventors: Gerd Kaibel, Lampertheim; Franz Josef Bröcker, Ludwigshafen; Manfred Stroezel, Ilvesheim, all of Germany

[73] Assignee: BASF Aktiengesellschaft, Ludwigshafen, Germany

[21] Appl. No.: 08/820,001

[22] Filed: Mar. 18, 1997

[30] Foreign Application Priority Data

Mar. 26, 1996 [DE] Germany .................. 196 11 976

[51] Int. Cl.$^6$ .................................................. C07C 49/00
[52] U.S. Cl. .............................................................. 568/568
[58] Field of Search ............................................. 568/568

[56] References Cited

U.S. PATENT DOCUMENTS

| | | | |
|---|---|---|---|
| 4,051,020 | 9/1977 | McDonald | 208/213 |
| 4,493,735 | 1/1985 | Flaschel et al. | 134/25.1 |
| 4,605,678 | 8/1986 | Brennan et al. | 518/700 |
| 4,731,229 | 3/1988 | Sperandio | 422/188 |
| 4,828,680 | 5/1989 | Greea et al. | 208/120 |
| 4,847,016 | 7/1989 | Goebel | 200/409 |
| 5,536,454 | 7/1996 | Fujii et al. | 261/97 |

FOREIGN PATENT DOCUMENTS

| | | |
|---|---|---|
| 068 862 | 1/1983 | European Pat. Off. . |
| 448 884 | 10/1991 | European Pat. Off. . |

OTHER PUBLICATIONS

*Ullmann's Encyclopaedie der technischen Chemie*, 4$^{th}$ Ed., 1973, vol. 3, pp. 494–518.

*Primary Examiner*—John Kight
*Assistant Examiner*—Raymond Covington
*Attorney, Agent, or Firm*—Keil & Weinkauf

[57] ABSTRACT

Catalytic reactions are carried out in a reactor which contains a liquid phase in which at least one catalyst is suspended, and which may additionally contain a gas phase, by a process in which the liquid phase and, if present, also the gas phase are fed, at least partly, through an apparatus having orifices or channels in the reactor, the hydraulic diameter of which orifices or channels is from 0.5 to 20 mm, preferably from 1 to 10 mm, particularly preferably from 1 to 3 mm.

5 Claims, 3 Drawing Sheets

PROCESS AND REACTOR FOR CARRYING OUT CONVERSION WITH CATALYSTS SUSPENDED IN LIQUIDS

The present invention relates to processes and reactors for carrying out catalytic reactions, in which a catalyst is suspended in a liquid phase. This phase may already contain a liquid or suspended solid reactant. Also frequently present is a gas phase, from which reactants are dissolved in the liquid phase. Typical reactions of this type are oxidations and hydrogenations.

Inter alia, bubble columns and stirred containers are suitable for carrying out such reactions. The technology for suspension reactions is described in detail in Ullmanns Encyclopädie der technischen Chemie, 4th Edition, 1973, Volume 3, pages 494 to 518. The basic problem of such reactions is to ensure sufficient contact between the reactants and the catalyst particles which are suspended in the liquid phase.

Suspension reactors require the supply of mechanical energy, which is introduced, for example, by means of stirrers, jets or ascending gas bubbles, in order to suspend the solid particles. However, increasing this mechanical energy supply beyond the magnitude required for suspending does not lead to a significant improvement in the mass transfer between the liquid and the suspended solid particles, since the achievable relative velocity exceeds the sedimentation rate only to an insignificant extent. The use of catalyst particles having larger particle sizes (from 1 to 10 mm) has been proposed for increasing this relative velocity, in particular in fluidized bed processes. Although these larger particles have the desired velocity relative to the surrounding liquid, their smaller surface area per unit volume on the other hand limits the conversion. The two effects frequently compensate one another so that the problem of increasing the conversion is not solved.

Higher relative velocities can be achieved only by dispensing with the suspension procedure in fixed-bed reactors. Instead of fixed beds, it is also possible to coat metal sheets or fabric with catalyst material, over which the liquid or gaseous phase flows. Such reactors are described in EP 068 862, EP 201 614 and EP 448 884. However, a disadvantage of these reactors is that the catalyst material can be regenerated only by replacing the coated components. This is expensive and, when there is a risk of contamination of the catalyst material by impure reactants, leads to expensive precautions, for example ultrapurification of the starting materials.

It is an object of the present invention to provide a process and a reactor for carrying out catalytic suspension reactions of the type described, having a higher space-time yield.

We have found that this object is achieved by the process described in the claims. In this process for carrying out catalytic reactions in a reactor which contains a liquid phase in which at least one catalyst is suspended, and which may additionally contain a gas phase, the liquid phase and, if present, the gas phase are fed, at least partly, ie. with at least a part of their volume or along a part of their route, through an apparatus having orifices or channels in the reactor, the hydraulic diameter of which orifices or channels is from 0.5 to 20 mm, preferably from 1 to 10 mm, particularly preferably from 1 to 3 mm. Reactants may be introduced either as liquid, as solid or as gas and may be dissolved in the liquid. In the present invention, the state of aggregation in which the reactants are fed in is in principle unimportant. The hydraulic diameter is defined as the quotient of 4 times the cross-section of the orifice and its circumference. The choice of the channel width which is ideal in the specific case depends in particular on the viscosity of the liquid passed through, the size of the suspended particles and the presence and type of a gas phase. The channel widths must be larger the more viscous the liquid. In the case of liquids having dynamic viscosities of from $10 \cdot 10^{-5}$ to $200 \cdot 10^{-5}$ Ns/m$^2$, hydraulic diameters of from 1 to 3 mm are optimum. In the presence of a gas phase, it is advisable to increase the channel diameter by from 10 to 50%.

In the novel process, the catalyst particles execute a greater movement relative to the liquid phase because they are decelerated relative to the surrounding liquid in the narrow orifices and channels. This deceleration may be caused by collisions with the channel walls or by brief retention of the particles on rough wall surfaces. In the novel process, suspended catalyst particles having a mean particle size of from 0.0001 to 2 mm, particularly preferably from 0.001 to 0.1 mm, more preferably from 0.005 to 0.05 mm, may be used. These particles with their large surface area per unit volume give good results because, owing to the passage through the narrow baffles, they can execute movements relative to the liquid. The result is that substantially higher space-time yields can be achieved. An experiment showed that even small relative movements of the catalyst particles or deceleration of only a small proportion of the catalyst particles lead to acceleration of the reaction.

The apparatus having orifices or channels for carrying out the feed phase may consist in a bed, a knitted fabric, an open-cell foam structure, preferably of plastic (eg. polyurethane or melamine resin) or ceramic, or a packing element as already known in principle, ie. in terms of its geometric shape, from distillation or extraction technology. Such packing elements, which have the advantage of a small pressure loss, are, for example, wire mesh packings of the designs Montz A3 and Sulzer BX, DX and EX. For the purposes of the present invention, however, the packings have in principle a hydraulic diameter which is substantially smaller, usually by a factor of from 2 to 10, than comparable baffles in the area of distillation or extraction technology. Wire mesh packings are particularly advantageous. This is presumably due to the fact that a part of the suspension does not follow the channels formed but passes through the mesh. Instead of mesh packings, packings of other woven, knitted or felted liquid-permeable materials can also be used in the present invention. In further suitable packings, flat metal sheets, preferably without perforations or other large orifices, are used, for example based on the designs Montz B1 and Sulzer Mellapak. Packings of expanded metal, for example packings of the type Montz BSH, are also advantageous. Here too, orifices, such as perforations, must be kept appropriately small. What is decisive for the suitability of a packing in the present invention is not its geometry but the orifice sizes or channel widths in the packing which are formed for the flow.

A preferred process is one in which the liquid phase and, where relevant, the gas phase are fed through orifices or channels whose wall materials have surface roughnesses of from 0.1 to 10, preferably from 0.5 to 5, times the mean particle size of the suspended catalyst particles. The roughness of the orifices or channel walls results in particularly good deceleration and hence relative movement of the suspended catalyst particles. These are presumably briefly held on the wall surfaces so that they enter the liquid stream again only after a delay. In the specific case, the preferred roughness of the material used depends on the size of the suspended catalyst particles.

In a preferred process, the liquid phase or the liquid/gas phase is fed through orifices or channels having metallic wall materials whose surfaces have a center line average value $R_a$ according to DIN 4768/1 of from 0.001 to 0.01 mm. Such metallic surfaces may be produced, for example, by thermal treatment of steels, for example Kanthal, in an oxygen atmosphere. Thus, not only macroscopic but also microscopic roughnesses are effective for the purposes of the present invention.

In a preferred process, the liquid phase is fed through the apparatus having orifices and channels at an empty tube velocity of from about 50 to 300, preferably from 150 to 200, m³/m²h. When a gas phase is simultaneously present, its empty tube velocity is preferably from 5 to 300, particularly preferably from 100 to 200, m³/m²h.

According to the invention, a reactor for carrying out catalytic reactions, as described in the claims, is also provided.

This reactor has means for feeding in and removing a liquid phase or suspension. If required, the reactor also has further feeding and removal means for a gas phase. The reactor contains at least one apparatus having orifices and channels which have a hydraulic diameter of from 0.5 to 20 mm, preferably from 1 to 10 mm, particularly preferably from 1 to 3 mm, the apparatus being installed and arranged in the reactor in such a way that the liquid phase and, where relevant, also the gas phase are fed, at least partly, through the orifices and channels during the reaction. Consequently, the more intensive movement of the liquid phase relative to the catalyst particles, which is described above, is achieved here too.

The present invention can be realized in various continuous or batchwise reactor designs, such as jet reactors, bubble columns, tubular reactors, tube-bundle reactors and stirred containers. In the case of a stirred container, the novel baffles may also be fastened directly to the stirrer shaft and at least partly perform the function of a stirring element. They may also act as flow spoilers. Apart from when used in stirred containers, the baffles presented above preferably, but not necessarily, fill the entire reactor. The novel reactor is preferably a vertically arranged bubble column through which, in the presence of a gas phase, flow is preferably cocurrent from bottom to top. Another preferred reactor is a heatable or coolable tube-bundle reactor in which the novel baffles are housed in the individual tubes. In the presence of a gas phase, flow through the reactor is preferably from bottom to top. A spiral or plate-type heat exchanger which contains the appropriate apparatuses is also preferred. A stirred container in which the baffles are integrated in the flow spoilers and/or stirring elements is likewise suitable as a reactor.

The suspended catalyst material can be introduced and separated off again with the aid of conventional methods (sedimentation, centrifuging, cake filtration, crossflow filtration).

Preferably, the apparatus having orifices or channels consists in a bed, a knitted fabric, an open-cell foam structure, which is preferably made of plastic or ceramic, or in a packing element from distillation or extraction technology. Statements made above in connection with the process are applicable in appropriate form here.

In a further preferred reactor, the orifices or channels of the apparatus have wall materials having surface roughnesses of from 0.1 to 10, preferably from 0.5 to 5, times the mean particle size of the suspended catalyst particles. In particular, it is possible to use metallic wall materials whose surfaces have a center line average value $R_a$ according to DIN 4768/1 of from 0.001 to 0.01 mm.

The suspended solids are separated off by the conventional separation methods, for example cake filtration or filtration through a cartridge filter. In a continuous reaction process, crossflow filtration proved particularly suitable.

The present invention is described in detail with reference to the following Figures.

The Figures show the following:

FIG. 1: Experimental setup for batchwise reaction process using a bubble column reactor modified according to the invention FIG. 2: Experimental setup for continuous reaction process using a bubble column reactor modified according to the invention FIG. 3: Experimental setup for continuous reaction process using a tube-bundle reactor modified according to the invention.

FIG. 1 shows, by way of example, an experimental setup using a batchwise bubble column reactor 1 in which a mesh packing 2 whose geometry is comparable with the Sulzer BX distillation packing is arranged according to the invention. To carry out the reaction, a liquid reactant containing suspended catalyst is first introduced via the filling line 3. A gaseous reactant is fed in via the connecting line 4 and is mixed in a mixing nozzle 5 with the circulated suspension, and this mixture is fed to the lower end of the reactor 1. The suspension is discharged from the reactor together with gas via the line 6 and passed into the separating vessel 7. From there, the gas is passed via a waste gas cooler 8 and via a pressure-maintaining means 9 into the waste gas line 10. The suspension passes from the separating vessel 7 via the line 11 into the pump 12, the heat exchanger 13, the mixing nozzle 5 and further into the reactor 1. After the end of the reaction, the suspension is discharged via the discharge line 14.

Figure 2:
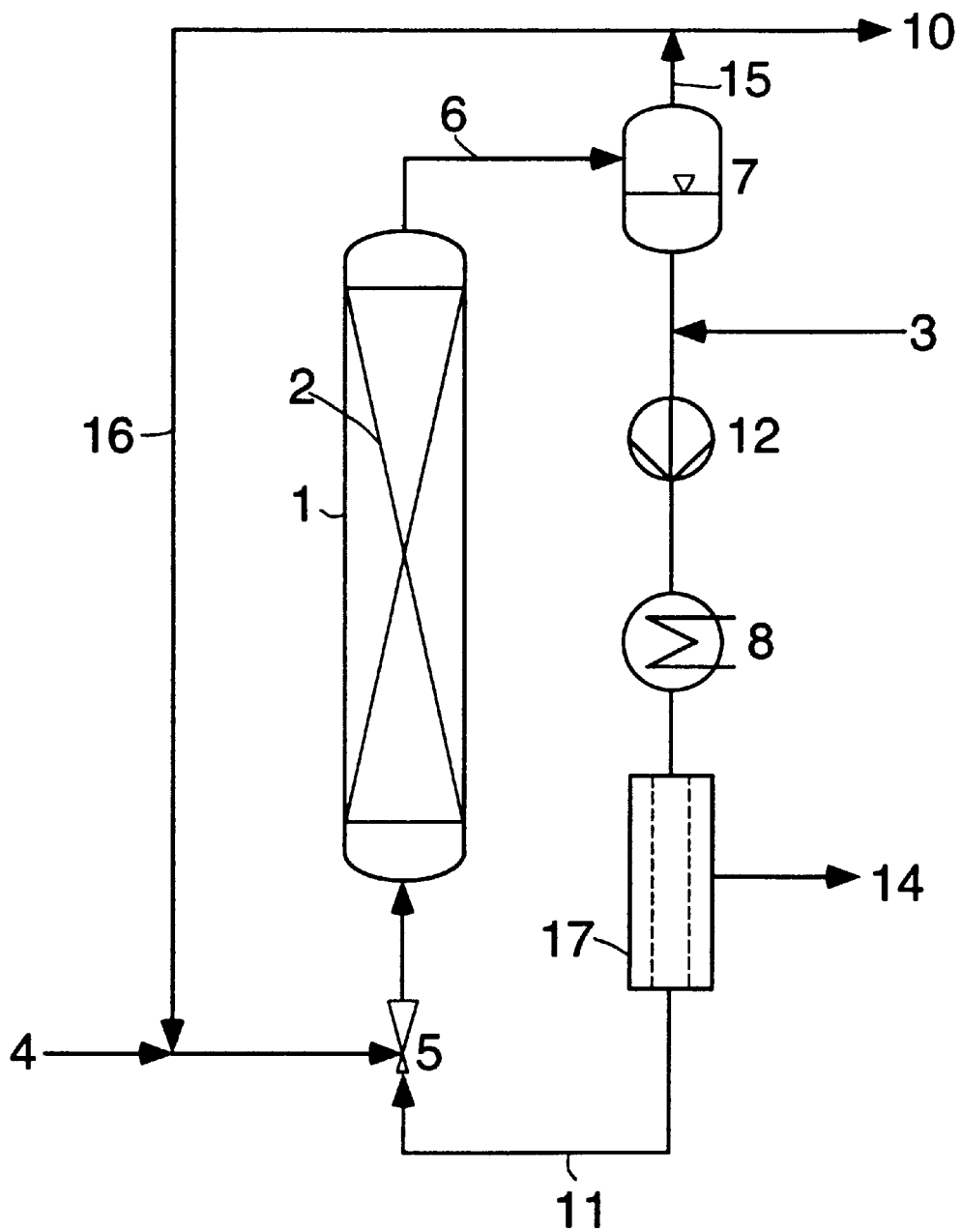

FIG. 2 shows a continuous reactor 1 having packings 2 which is additionally operated, via the lines 15 and 16, with recycled gas which, together with fresh gas 4, is mixed by means of the mixing nozzle 5 into the circulated suspension 11. The reactor discharge is fed via the line 6 into the separating vessel 7 in which the gas phase is separated off and removed via the line 15. To limit the increase in the level of gaseous impurities, a bleed-stream of this amount of gas is removed via the line 10, and the remaining amount of gas is recycled to the reactor via the line 16. Only liquid reactant is introduced via the line 3. The suspended catalyst remains in the reactor system by virtue of the fact that it is retained by means of a crossflow filter 17 and only catalyst-free liquid 14 emerges and is removed.

Figure 3:
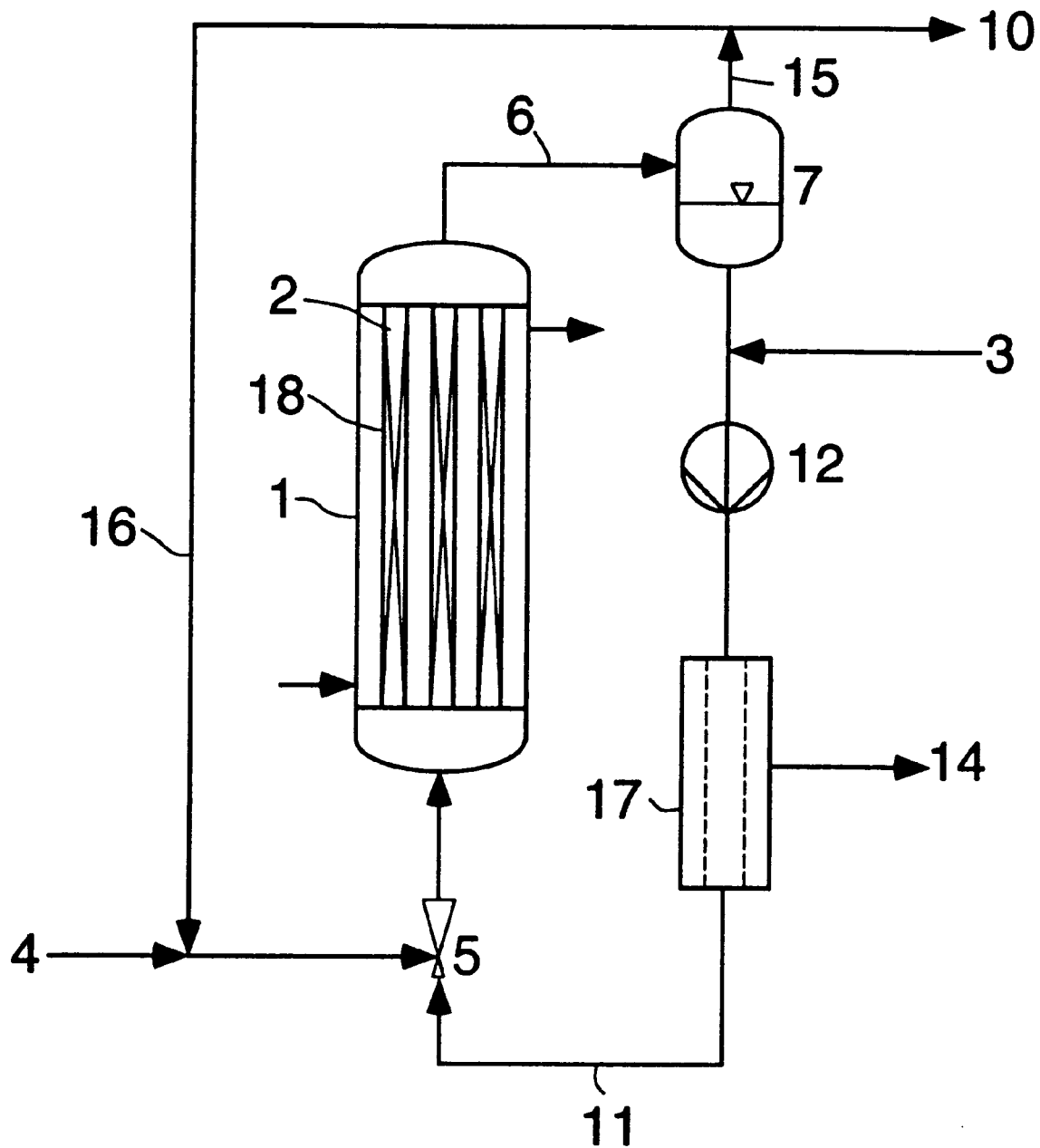

FIG. 3 shows the embodiment which is preferably to be used in the case of fast reactions with high heat of reaction and in which the reactor 1 has the design of a tube-bundle heat exchanger and possesses tube bundles 18 in which wire mesh packings 2 are arranged. The heat exchanger 8 present in FIGS. 1 and 2 may be dispensed with in this embodiment. It may be retained to perform the function of a heater at the beginning of the reaction if the reactor is to be fed only with coolant. The functions of the parts 4, 5, 6, 7, 10, 12, 14, 16 and 17 correspond to those in FIG. 2.

EXAMPLES

The advantages of the invention described are illustrated below with reference to Examples of the hydrogenation of hydrodehydrolinalool to hydrolinalool and further to tetrahydrolinalool. The triple bond is hydrogenated first to a double bond and finally to a single bond.

The reaction was carried out on the one hand in a conventional stirred container having a three-blade gassing stirrer (1 l volume, 54 mm stirrer diameter, 1000 rpm) and flow spoilers.

On the other hand, a bubble column (400 mm height, 40 mm diameter) equipped with a mesh packing was used according to the present invention for the hydrogenation. The experimental setup corresponded to FIG. 1. The geometry of the packing corresponded to a commercial mesh packing of the type Sulzer BX but the wire mesh had a wire thickness of 0.112 mm and was therefore finer and the gaps were narrower. The bend width was 1 mm and the angle of inclination of the bends relative to the vertical was 60°. The surface area of the packing per unit volume was 2200 $m^2/m^3$, these data being based only on the geometric surface area of the mesh analogously to flat sheets. The liquid containing the suspended catalyst and the gas was introduced from below into the reactor containing the packing at an empty tube velocity of 175 $m^3/m^2h$.

In both cases, the reaction was carried out batchwise under 1.1 bar. The catalyst used was a ZnO-doped palladium catalyst on a $CaCO_3$ carrier which had a mean particle size of about 0.01 mm. The amount of hydrodehydrolinalool used was 650 g in the Comparative Experiments in the stirred container and 840 g in the experiments using the novel reactor. The hydrogenation was carried out at 80° C.

Example 1

Packed bubble column containing 0.15% by weight of catalyst. The hydrogenation of the triple bond was complete after 1.75 hours and that of the double bond after 4 hours.

Example 2

Packed bubble column containing 0.31% by weight of catalyst. The hydrogenation times were about the same as those in Example 1.

Comparative Example 1

Stirred container containing 0.15% by weight of catalyst. The hydrogenation of the triple bond was complete after 5 hours and that of the double bond after 11 hours.

Comparative Example 2

Stirred container containing 0.31% by weight of catalyst. The corresponding hydrogenation times were 3.5 and 7 hours.

Comparative Example 3

Stirred container containing 0.77% by weight of catalyst. The hydrogenation times decreased to 3 and 5.5 hours.

The Comparative Experiments show that, in a conventional reactor, the space-time yield increases with the amount of catalyst introduced. This means that the reaction rate is controlled by the mass transfer. On the other hand, when the novel process is used, the reaction times remain unchanged if the amount of catalyst added is increased. This shows that the reaction rate is no longer controlled by the mass transfer. The maximum possible reaction rate is determined in the novel experiments by the mass transfer from the gas phase to the liquid. It is reached even at relatively low catalyst concentrations.

We claim:

1. A process for carrying out catalytic reactions in a reactor which contains a liquid phase in which at least one catalyst is suspended, and which may additionally contain a gas phase, wherein the liquid phase and, where relevant, the gas phase are fed, at least partly, through an apparatus having orifices or channels in the reactor, the hydraulic diameter of which orifices or channels is from 0.5 to 20 mm, preferably from 1 to 10 mm, particularly preferably from 1 to 3 mm, wherein said orifices or channels have wall materials which have surface roughnesses of from 0.1 to 10, preferably from 0.5 to 5, times the mean particle size of the suspended catalyst particles, and wherein the liquid phase is fed through the apparatus having orifices or channels at an empty tube velocity of from 50 to 300, preferably from 150 to 200, $m^3/m^2h$.

2. A process as claimed in claim 1, wherein suspended catalyst particles having a mean particle size of from 0.0001 to 2 mm, preferably from 0.001 to 0.1 mm, particularly preferably from 0.005 to 0.05 mm, are used.

3. A process as claimed in claim 1, wherein a bed, a knitted fabric, an open-cell foam structure, preferably comprising plastic or ceramic, or a packing element as known in principle from distillation or extraction technology is used as the apparatus having orifices or channels.

4. A process as claimed in claim 1, wherein the liquid phase and, where relevant, the gas phase are fed through orifices or channels having metallic wall materials whose surfaces have a center line average value $R_a$ according to DIN 4768/1 of from 0.001 to 0.01 mm.

5. A process as claimed in claim 1, wherein any gas phase simultaneously present is fed through the apparatus having orifices or channels at an empty tube velocity of, preferably, from 5 to 300, particularly preferably from 100 to 200, $m^3/m^2h$.

* * * * *